US009983213B2

(12) United States Patent
Hess et al.

(10) Patent No.: US 9,983,213 B2
(45) Date of Patent: May 29, 2018

(54) IDENTIFICATION OF SUBJECTS BEING SUSCEPTIBLE TO ANTI-ANGIOGENESIS THERAPY

(75) Inventors: Georg Hess, Mainz (DE); Andrea Horsch, Mannheim (DE); Dietmar Zdunek, Tutzing (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 94 days.

(21) Appl. No.: 13/010,183

(22) Filed: Jan. 20, 2011

(65) Prior Publication Data

US 2011/0113864 A1 May 19, 2011

Related U.S. Application Data

(63) Continuation of application No. PCT/EP2009/059505, filed on Jul. 23, 2009.

(30) Foreign Application Priority Data

Jul. 23, 2008 (EP) ..................................... 08161014

(51) Int. Cl.
| | |
|---|---|
| G01N 33/53 | (2006.01) |
| A61P 35/00 | (2006.01) |
| G01N 33/68 | (2006.01) |
| C07K 16/18 | (2006.01) |
| C07K 14/47 | (2006.01) |
| C07K 14/475 | (2006.01) |
| C07K 14/515 | (2006.01) |
| C07K 16/22 | (2006.01) |

(52) U.S. Cl.
CPC .......... *G01N 33/6887* (2013.01); *A61P 35/00* (2018.01); *G01N 33/53* (2013.01); *C07K 14/47* (2013.01); *C07K 14/475* (2013.01); *C07K 16/18* (2013.01); *C07K 16/22* (2013.01); *G01N 2333/4712* (2013.01); *G01N 2333/58* (2013.01); *G01N 2800/32* (2013.01); *G01N 2800/52* (2013.01)

(58) Field of Classification Search
None
See application file for complete search history.

(56) References Cited

U.S. PATENT DOCUMENTS

| 5,744,305 A | 4/1998 | Fodor et al. |
| 6,582,959 B2 | 6/2003 | Kim |
| 6,703,020 B1 | 3/2004 | Thorpe et al. |
| 2002/0051978 A1 | 5/2002 | Roth et al. |
| 2003/0190317 A1 | 10/2003 | Baca et al. |

FOREIGN PATENT DOCUMENTS

| EP | 0648228 B1 | 11/1998 |
| EP | 0666868 B1 | 4/2002 |
| WO | 98/45331 A3 | 10/1998 |
| WO | 00/54770 A1 | 9/2000 |
| WO | 02/083913 A1 | 10/2002 |
| WO | 02/089657 A3 | 11/2002 |
| WO | 2005/000900 A1 | 1/2005 |
| WO | 2005/044853 A3 | 5/2005 |
| WO | 2006/052788 A3 | 5/2006 |
| WO | 2008/017928 A3 | 2/2008 |
| WO | 2008/061978 A3 | 5/2008 |
| WO | 2008/063932 A3 | 5/2008 |

OTHER PUBLICATIONS

Kilickap et al, 2005 (Annals of Oncology. 16: 798-804).*
International Search Report issued Oct. 14, 2009 in PCT Application No. PCT/EP2009/059505.
International Preliminary Report on Patentability issued Dec. 10, 2010 in PCT/EP2009/059505.
Anderson, Page A. W. et al., "Molecular Basis of Human Cardiac Troponin T Isoforms Expressed in the Developing, Adult, and Failing Heart," Circulation Research, 1995, pp. 681-686, vol. 76.
Bonow, Robert O., "New Insights Into the Cardiac Natriuretic Peptides," Circulation, 1996, pp. 1946-1950, vol. 93.
Chen, Yvonne et al., "Selection and Analysis of an Optimized Anti-VEGF Antibody: Crystal Structure of an Affinity-matured Fab in complex with Antigen," Journal of Molecular Biology, 1999, pp. 865-881, vol. 293.
Chien, Kenneth R., "Herceptin and the Heart—A Molecular Modifier of Cardiac Failure," The New England Journal of Medicine, Feb. 23, 2006, pp. 789-790, vol. 354, No. 8.
Dolci, Alberto et al., "Biochemical Markers for Prediction of Chemotherapy-Induced Cardiotoxicity," American Journal of Clinical Pathology, 2008, pp. 688-695, vol. 130.
Dolci, Alberto et al., "Biochemical markers for predicting chemotherapy-induced cardiotoxicity: Systematic review of the literature and recommendations for use," Giornale Italiano di Cardiologia, Sep. 2006, pp. 604-611, vol. 7, No. 9.
Ferrieres, Gaelle et al., "Human cardiac troponin I: precise identification of antigenic epitopes and prediction of secondary structure," Clinical Chemistry, 1998, pp. 487-493, vol. 44, No. 3.
Fischer, Christian et al., "Anti-PlGF Inhibits Growth of VEGF(R)-Inhibitor-Resistant Tumors without Affecting Healthy Vessels," Cell, Nov. 2, 2007, pp. 463-475, vol. 131.
Germanakis, Ioannis et al., "Troponins and Natriuretic Peptides in the Monitoring of Anthracycline Cardiotoxicity," Pediatric Blood and Cancer, Sep. 2008, pp. 327-333, vol. 51, No. 3.
Karl, J. et al., "Development of a novel, N-Terminal-proBNP (NT-proBNP) assay with a low detection limit," Scandinavian Journal of Clinical and Laboratory Investigation, 1999, pp. 177-181, vol. 59, Supplement 230.

(Continued)

*Primary Examiner* — Zachary Howard
(74) *Attorney, Agent, or Firm* — Dinsmore & Shohl LLP

(57) ABSTRACT

The present invention relates to a method for identifying a subject being susceptible to anti-angiogenesis therapy based in determining the amount of a cardiac troponin in a sample of the subject and comparing the amount to a suitable reference amount. Also encompassed by the present invention are kits and devices adapted to carry out the method of the present invention.

12 Claims, 1 Drawing Sheet

(56) References Cited

OTHER PUBLICATIONS

Langer, B. et al., "Prospective investigation of the significance of cardiac markers, NT-pro Brain Natriuretic Peptide (NT-proBNP) and Troponin T (TnT), in the HERCULES study of epirubicin/cyclophosphamide with or without trastuzumab (Herceptin®)," EJC Supplements, Mar. 18, 2004, pp. 143, vol. 2, No. 3.

Mego, M. et al., "Increased cardiotoxicity of sorafenib in sunitinib-pretreated patients with metastatic renal cell carcinoma," Annals of Oncology, Nov. 2007, pp. 1906-1907, vol. 18, No. 11.

Mueller, Thomas et al., "Long-term stability of endogenous B-type natriuretic peptide (BNP) and amino terminal proBNP (NT-proBNP) in frozen plasma samples," Clinical Chemistry and Laboratory Medicine, 2004, pp. 942-944, vol. 42, No. 8.

Needleman, Saul B. and Wunsch, Christian D., "A General Method Applicable to the Search for Similarities in the Amino Acid Sequence of Two Proteins," Journal of Molecular Biology, 1970, pp. 443-453, vol. 48.

Nolan, John P. and Sklar, Larry A., "Suspension array technology: evolution of the flat-array paradigm," Trends in Biotechnology, Jan. 2002, pp. 9-12, vol. 20, No. 1.

O'Brien, Peter James, "Blood cardiac troponin in toxic myocardial injury: archetype of a translational safety biomarker," Expert Review of Molecular Diagnostics, 2006, pp. 685-702, vol. 6, No. 5.

O'Reilly, Michael S. et al., "Angiostatin: A Novel Angiogenesis Inhibitor That Mediates the Suppression of Metastases by a Lewis Lung Carcinoma," Cell, Oct. 21, 1994, pp. 315-328, vol. 79.

O'Reilly, Michael S. et al., "Endostatin: An Endogenous Inhibitor of Angiogenesis and Tumor Growth," Cell, Jan. 24, 1997, pp. 277-285, vol. 88.

Pearson, William R. and Lipman, David J., "Improved tools for biological sequence comparison," Proceedings of the National Academy of Sciences, Apr. 1988, pp. 2444-2448, vol. 85.

Popkov, Mikhail et al., "Human/mouse cross-reactive anti-VEGF receptor 2 recombinant antibodies selected from an immune b9 allotype rabbit antibody library," Journal of Immunological Methods, 2004, pp. 149-164, vol. 288.

Smith, M. W. et al., "Delayed metabolism of human brain natriuretic peptide reflects resistance to neutral endopeptidase," Journal of Endocrinology, 2000, pp. 239-246, vol. 167.

Smith, Temple F. and Waterman, Michael S., "Comparison of Biosequences," Advances in Applied Mathematics, 1981, pp. 482-489, vol. 2.

Wu, Alan H. B. et al., "Analytical and Clinical Evaluation of the Bayer ADVIA Centaur Automated B-Type Natriuretic Peptide Assay in Patients with Heart Failure: A Multisite Study," Clinical Chemistry, 2004, pp. 867-873, vol. 50, No. 5.

Yeo, Kiang-Teck J. et al., "Multicenter evaluation of the Roche NT-proBNP assay and comparison to the Biosite Triage BNP assay," Clinica Chimica Acta, 2003, pp. 107-115, vol. 338.

Cardinale, Daniela et al., "Prevention of High-Dose Chemotherapy-Induced Cardiotoxicity in High-Risk Patients by Angiotensin-Converting Enzyme Inhibition," Circulation, 2006, pp. 2474-2481, vol. 114.

Force, Thomas, et al., "Molecular mechanisms of cardiotoxicity of tyrosine kinase inhibition," Nature, 2007, pp. 332-344, vol. 7.

Jones, Lee W. et al., "Early Breast Cancer Therapy and Cardiovascular Injury," Journal of the American College of Cardiology, 2007, pp. 1435-1441, vol. 50, No. 15.

Pouna, Paul et al., "Development of the model of rat isolated perfused heart for the evaluation of anthracycline cardiotoxicity and its circumvention," British Journal of Pharmacology, 1996, pp. 1593-1599, vol. 117.

Trastuzumab, from Wikipedia, http://en.wikipedia.org/wiki/Trastuzumab, retrieved Jan. 16, 2009, 6 pages.

Braunwald, Eugene, MD et al, "ACC/AHA Guidelines for the Management of Patients with Unstable Angina and Non-ST-Segment Elevation Myocardial Infarction"; Journal of the American College of Cardiology; vol. 36, No. 3, 2000, pp. 970-1062.

Omland, Torbjorn MD et al, "A Sensitive Cardiac Troponin T Assay in Stable Coronary Artery Disease"; N Engl J Med. Dec. 24, 2009; 361(26): 2538-2547.

Traina, Tiffany A. MD et al, "Bevacizumab for Advanced Breast Cancer"; Hematol Oncol Clinic N Am 21 (2007) 303-319.

Murakami, "Multi-Biomarker Strategy for Acute Coronary Syndrome"; J Clin Exper Med 2008; 224 (5): 313-317.

Adamcova, Michaela et al., "Troponin as a marker of myocardial damage in drug-induced cardiotoxicity," Expert Opinion on Drug Safety, 2005, pp. 457-472, vol. 4, No. 3.

Cardinale, Daniela et al., "Prognostic Value of Troponin I in Cardiac Risk Stratification of Cancer Patients Undergoing High-Dose Chemotherapy," Circulation, 2004, pp. 2749-2754, vol. 109.

\* cited by examiner

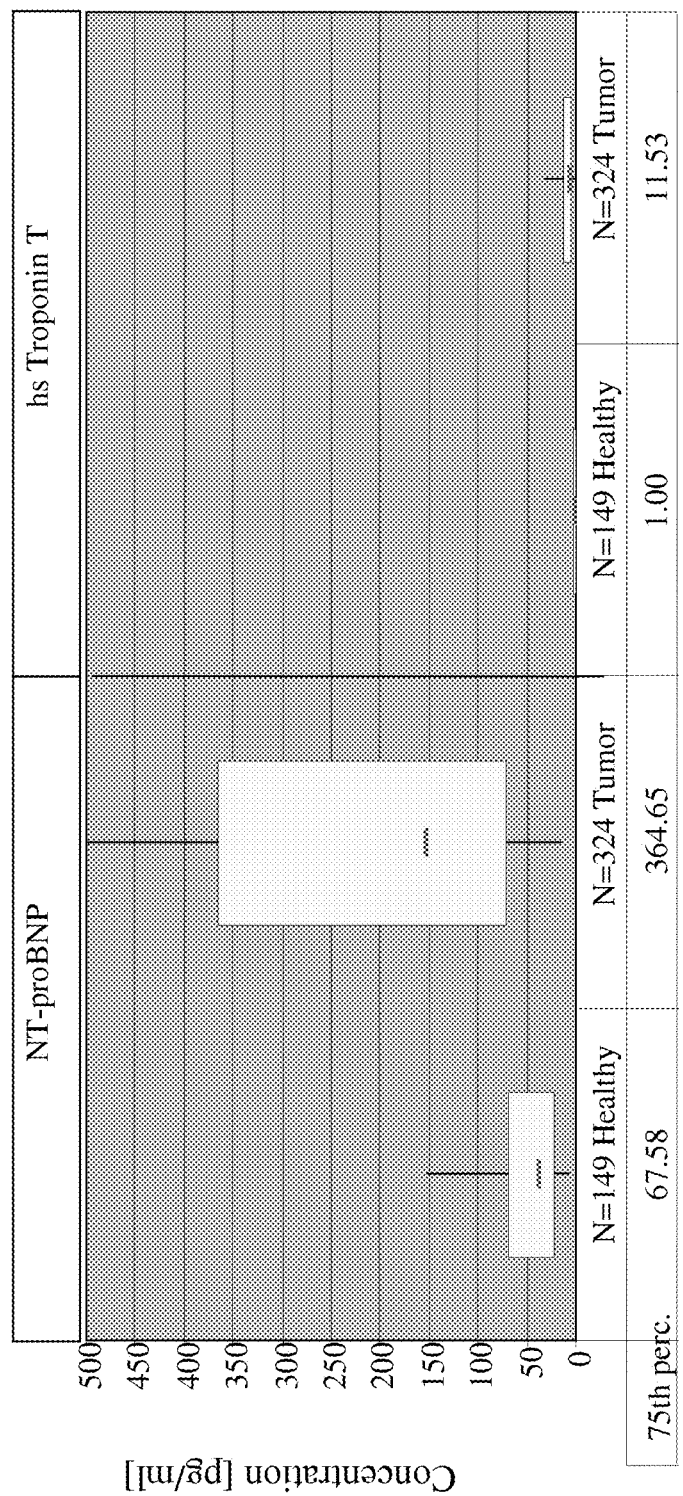

US 9,983,213 B2

IDENTIFICATION OF SUBJECTS BEING SUSCEPTIBLE TO ANTI-ANGIOGENESIS THERAPY

RELATED APPLICATIONS

This application is a continuation of PCT/EP2009/059505 filed Jul. 23, 2009 and claims priority to EP 08161014.9 filed Jul. 23, 2008.

FIELD OF THE INVENTION

The present invention relates to a method for identifying a subject being susceptible to anti-angiogenesis therapy based in determining the amount of a cardiac troponin in a sample of said subject and comparing said amount to a suitable reference amount. Also encompassed by the present invention are kits and devices adapted to carry out the method of the present invention.

BACKGROUND OF THE INVENTION

An aim of modern medicine is to provide personalized or individualized treatment regimens. Those are treatment regimens which take into account a patient's individual needs or risks. Hyperproliferative disorders have in many cases a severe impact on the human or animal physiology. Many severe diseases, such as cancer, are caused by undesired, enhanced proliferation of cells. Specifically, cancer diseases comprise some of the most life threatening medical conditions, such as lung carcinomas which belong to the leading causes of human cancer death.

Various approaches for cancer therapy exist, e.g., surgery, chemotherapy, radiation therapy, and immunotherapy. A new, very promising cancer therapy is anti-angiogenesis therapy. The principle underlying anti-angiogenesis therapy is that tumors can grow only if new blood vessels are being formed within the blood vessels. By stopping the growth of blood vessels within the tumors with angiogenesis inhibitors, the means by which tumors can extend themselves and spread inside the body are significantly reduced. Administration of the angiogenesis inhibitor Bevacizumab (Avastin) was the first U.S. Food and Drug Administration (FDA)-approved biological therapy designed to inhibit the formation of new blood vessels in tumors. Bevacizumab itself is a monoclonal antibody against the vascular endothelial growth factor (VEGF). It was shown, e.g., that Bevacizumab significantly improves survival in metastatic colorectal cancer. The FDA has also approved other anti-angiogenic pharmaceuticals for cancer therapy, e.g. for multiple myeloma, mantle cell lymphoma, gastrointestinal stromal tumors, and kidney cancer. More anti-angiogenesis cancer therapies are awaiting approval.

The great beneficial effects of treating cancer patients with anti-angiogenic drugs, however, are being hampered by some problems. There is evidence that a therapy which inhibits new vessel formation has adverse side effects (particularly cardiovascular complications) and, therefore, may put some patients at risk. Accordingly, it was shown that, e.g., sorafenib induces acute coronary syndromes in 2.9% of patients treated with sorafenib (2007, Annals of Oncology, Volume 18. No. 12, 1906-1907).

Therefore, measures and means are required in order to (i) identify those subjects that are susceptible to a therapy with anti-angiogenic drugs and to (ii) identify those subjects which would be at elevated risk of heart failure and/or acute cardiovascular events as a consequence of a future intake of anti-angiogenic drugs.

However, such means and measures have not been described yet. Thus, the technical problem underlying the present invention can be seen as the provision of means and methods for complying with the aforementioned needs.

The technical problem is solved by the embodiments characterized in the claims and herein below.

SUMMARY OF THE INVENTION

Accordingly, the present invention relates to a method for identifying a subject being susceptible to anti-angiogenesis therapy comprising the steps of
  a) determining the amount of a cardiac troponin in a sample of said subject,
  b) comparing the amount of a cardiac troponin as determined in step a) with a suitable reference amount for a cardiac troponin, and
  c) identifying a subject being susceptible to anti-angiogenesis therapy.

The method of the present invention allows assessing whether a subject who is in need for an anti-anti-angiogenesis therapy, will be susceptible to said therapy. Preferably, by carrying out the method of the present invention decisions can be made whether said anti-angiogenesis therapy shall be initiated or not.

The method of the present invention, preferably, is an in vitro method. Moreover, it may comprise steps in addition to those explicitly mentioned above. For example, further steps may relate to sample pre-treatments or evaluation of the results obtained by the method. The method of the present invention may be also used for confirmation, and subclassification of a subject in need of an anti-angiogenesis therapy. The method may be carried out manually or assisted by automation. Preferably, step (a), (b) and/or (c) may in total or in part be assisted by automation, e.g., by a suitable robotic and sensory equipment for the determination in step (a) and/or (b) or a computer-implemented comparison in step (c).

BRIEF DESCRIPTION OF THE FIGURE

FIG. 1 shows: NT-proBNP and troponin T in subjects suffering from cancer and in healthy individuals. Median amounts for the 75th percentile are indicated; n=number of individuals.

DETAILED DESCRIPTION OF THE INVENTION

The term "identifying" as used herein means assessing whether a subject will be susceptible for anti-angiogenesis therapy or not. It is to be understood that a subject who is susceptible to anti-angiogenesis therapy, preferably, will not be at elevated risk of suffering from an adverse side effect caused by said therapy (particularly, of heart failure, an acute cardiovascular event, hypertension, or other vascular events such as stroke, peripheral arterial disease, and/or abdominal angina) as a consequence of the therapy, whereas a subject who is not susceptible to anti-angiogenesis therapy would be of elevated risk of suffering from the aforementioned adverse side effects as a consequence of said anti-angiogenesis treatment regimen (if said treatment regimen would be initiated). As will be understood by those skilled in the art, such an assessment is usually not intended to be correct for all (i.e. 100%) of the subjects to be identified. The term, however, requires that a statistically significant portion of subjects can be identified (e.g. a cohort in a cohort study). Whether a portion is statistically significant can be determined without further ado by the person skilled in the art using various well known statistic evaluation tools, e.g., determination of confidence intervals, p-value determination, Student's t-test, Mann-Whitney test etc. Details are found in Dowdy and Wearden, Statistics for Research, John Wiley & Sons, New York 1983. Preferred confidence intervals are at least 90%, at least 95%, at least 97%, at least 98% or at least 99%. The p-values are, preferably, 0.1, 0.05, 0.01, 0.005, or 0.0001. More preferably, at least 60%, at least 70%, at least 80% or at least 90% of the subjects of a population can be properly identified by the method of the present invention.

The term "subject" as used herein relates to animals, preferably mammals, and, more preferably, humans.

However, it is envisaged in accordance with the aforementioned method of the present invention that the subject shall be "in need of an anti-angiogenesis therapy". However, said subject shall not have received an anti-angiogenesis therapy at the time at which the sample is obtained. Thus, the subject shall not be on anti-angiogenesis therapy when the sample is obtained.

"A subject in need of anti-angiogenesis therapy, preferably, is subject who suffers from cancer, and more preferably, from metastatic cancer. It is to be understood that said cancer may be any type of cancer such as neuroblastoma, intestine carcinoma such as rectum carcinoma, colon carcinoma, adenomatous polyposis carcinoma and hereditary non-polyposis colorectal cancer, esophageal carcinoma, labial carcinoma, larynx carcinoma, hypopharynx carcinoma, tongue carcinoma, salivary gland carcinoma, gastric carcinoma, adenocarcinoma, medullary thyroid carcinoma, papillary thyroid carcinoma, follicular thyroid carcinoma, anaplastic thyroid carcinoma, renal carcinoma, kidney parenchym carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, brain tumors such as glioblastoma, astrocytoma, meningioma, medulloblastoma and peripheral neuroectodermal tumors, hepatocellular carcinoma, gall bladder carcinoma, bronchial carcinoma, small cell lung carcinoma, non-small cell lung carcinoma, multiple myeloma, basalioma, teratoma, retinoblastoma, choroidea melanoma, seminoma, rhabdomyosarcoma, craniopharyngeoma, osteosarcoma, chondrosarcoma, myosarcoma, liposarcoma, fibrosarcoma, Ewing sarcoma and plasmocytoma. Preferably, said cancer is A variety of cancer types are known in the art comprise neuroblastoma, intestine carcinoma such as rectum carcinoma, colon carcinoma, familiary adenomatous polyposis carcinoma and hereditary non-polyposis colorectal cancer, esophageal carcinoma, labial carcinoma, larynx carcinoma, hypopharynx carcinoma, tong carcinoma, salivary gland carcinoma, gastric carcinoma, adenocarcinoma, medullary thyroid carcinoma, papillary thyroid carcinoma, follicular thyroid carcinoma, anaplastic thyroid carcinoma, renal carcinoma, kidney parenchym carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, brain tumors such as glioblastoma, astrocytoma, meningioma, medulloblastoma and peripheral neuroectodermal tumors, Hodgkin lymphoma, non-Hodgkin lymphoma, Burkitt lymphoma, acute lymphatic leukemia (ALL), chronic lymphatic leukemia (CLL), acute myeolid leukemia (AML), chronic myeloid leukemia (CML), adult T-cell leukemia lymphoma, hepatocellular carcinoma, gall bladder carcinoma, bronchial carcinoma, small cell lung carcinoma, non-small cell lung carcinoma, multiple myeloma, basalioma, teratoma, retinoblastoma, choroidea melanoma, seminoma, rhabdomyosarcoma, craniopharyngeoma, osteosarcoma, chondrosarcoma, myosarcoma, liposarcoma, fibrosarcoma, Ewing sarcoma and plasmocytoma.

It is particularly contemplated that said cancer is selected from the group consisting of metastatic colon cancer (also known as colorectal cancer), non-small cell lung cancer, renal cell carcinoma, glioblastoma multiforme, ovarian cancer, metastatic prostate cancer, and pancreatic cancer.

It is also envisaged by the method of the present invention that the subject in need of an anti-angiogenesis therapy may suffer from diabetic retinopathy, age-related macular degeneration, rheumatoid arthritis or psoriasis.

Moreover, it is envisaged by the present invention that the subject may be at risk to suffer from a cardiovascular complication, or a subject who suffers from a cardiovascular complication, respectively. Said cardiovascular complication may be clinically apparent, but may be also clinically not apparent, yet. The method of the present invention is, particularly, beneficial for these subjects, since anti-angiogenesis therapy may deteriorate an already existing cardiovascular complication or increase the risk thereof. The method of the present invention allows to identify those subjects whose cardiovascular condition would deteriorate or would not deteriorate as a consequence of anti-angiogenesis therapy.

A subject suffering from a "cardiovascular complication", preferably, may be a subject suffering from any cardiovascular disease, dysfunction, or event known to the person skilled in the art. Particularly, said subject may show clinical symptoms for ischemic heart disease, heart failure, coronary artery disease (particularly, stable coronary artery disease), ischemic heart disease, dilated cardiomyopathy, stable angina, congestive heart failure.

The subject suffering from a cardiovascular complication may show clinical symptoms (e.g. dyspnea, chest pain, see also NYHA classification below). Specifically, symptoms of cardiovascular diseases have been classified into a functional classification system according to the New York Heart Association (NYHA). Patients of Class I have no obvious symptoms of cardiovascular disease. Physical activity is not limited, and ordinary physical activity does not cause undue fatigue, palpitation, or dyspnea. Patients of class II have slight limitation of physical activity. They are comfortable at rest, but ordinary physical activity results in fatigue, palpitation, or dyspnea. Patients of class III show a marked limitation of physical activity. They are comfortable at rest, but less than ordinary activity causes fatigue, palpitation, or dyspnea. Patients of class IV are unable to carry out any physical activity without discomfort. They show symptoms of cardiac insufficiency at rest. If any physical activity is undertaken, discomfort is increased. Another characteristic of cardiovascular complication can be the "left ventricular ejection fraction" (LVEF) which is also known as "ejection fraction". People with a healthy heart usually have an unimpaired LVEF, which is generally described as above 50%. Most people with a systolic heart disease which is symptomatic, generally, have an LVEF of 40% or less.

Preferably, a subject suffering from a cardiovascular complication in accordance with the present invention can be allocated to an intermediated NYHA class, preferably, to NYHA class I, II or III and, most preferably, to NYHA class II.

It is also contemplated that the subject in need for anti-angiogenesis treatment is a subject with an undetected cardiovascular complication (undetected at the time at which the method of the present invention is carried out; more precisely, at the moment at which the sample to be analyzed is obtained).

The term "anti-angiogenesis therapy" as used herein, preferably, encompasses those treatment regimens which aim to reduce or inhibit the formation of blood vessels (preferably of new blood vessels, more preferably, of blood vessels that deliver blood to the myocardium, and, and, thus supply the myocardium), and, thus, encompasses those treatment regimens which are capable of inhibiting angiogenesis, particularly of vessels that deliver blood to the myocardium. Said treatment regimens are well known in the art and, preferably, reduce/inhibit the formation of new vessels from pre-existing vessels and/or from endothelial precursor cells. Preferably, an anti-angiogenesis therapy relates to a drug-based anti-angiogenesis therapy.

Preferably, drugs to be used for anti-angiogenesis therapy only have low cardiotoxicity, more preferably, said drugs do not have any cardiotoxicity, and, thus, are not cardiotoxic. In the context of the present invention a drug, preferably, is considered as being cardiotoxic, if said drug induces myocardial cell damage and/or necrosis when myocardial cells are contacted with said drug. A cardiotoxic drug in the context of the present invention is a drug that induces cardiac cell damage and/or apoptosis (preferably, myocardial cell damage and/or apoptosis of myocardial cells) when directly contacted with myocardial cells. How to determine whether a drug induces myocardial cell damage and/or apoptosis upon direct contact is well known in the art.

The method of the present invention is particularly advantageous for subjects which are treated with a VEGF antagonist (preferably, VEGF-A antagonists), particularly with antibodies specific for VEGF (preferably, specific for VEGF-A). Accordingly, the anti-angiogenesis therapy, preferably, is by intake of VEGF antagonists, more preferably by intake of antibodies against VEGF, most preferably by intake of antibodies against VEGF-A. The term "VEGF antagonist", preferably, refers to a molecule being capable of inhibiting, reducing or interfering with VEGF activities including its binding to one or more VEGF receptors, particularly with the VEGF receptor 1 or 2 (VEGFR-1 or VEGFR-2). WO/2008/063932, which hereby is incorporated by reference in its entirety with respect to the disclosure content, lists a variety of VEGF antagonists. Preferably, the term the anti-angiogenesis therapy is by anti-VEGF antibodies that specifically bind VEGF and thereby negatively affect interaction with at least one VEGF receptor, particularly with the VEGF receptor 1 or 2 (VEGFR-1 or VEGFR-2). VEGF antagonists, preferably, also encompass antisense molecules that target VEGF, RNA aptamers that target VEGF, and ribozymes that target VEGF or VEGF receptors (particularly VEGFR-1 or 2).

Anti-VEGF antibodies include, but are not limited to, antibodies A4.6.1, bevacizumab (Avastin®), ranibizumab (Lucentis®, see WO98/45331 or Chen et al J Mol Biol 293:865-881 (1999)) G6, B20, 2C3, and others as described in, for example, US2003/0190317, U.S. Pat. Nos. 6,582,959 and 6,703,020; WO98/45332; WO2005/044853; EP 0666868B1; and Popkov et al, Journal of Immunological Methods 288:149-164 (2004). Most preferably, the anti-VEGF antibody of the invention is bevacizumab.

Also contemplated by the method of the present invention as suitable for anti-angiogenesis therapy are antibodies against tumor necrosis factor alpha, low molecular weight tyrosine kinase inhibitors, matrix metalloproteinase inhibitors (Marimastat, AG3340, COL-3, Neovastat, BMS-275291)), drugs that inhibit cell proliferation and cell migration of endothelial cells, drugs that negatively regulate stimulators of angiogenesis, drugs that stimulate the formation of endogenous angiogenesis inhibitors, drugs that inhibit binding of angiogenesis stimulators, drugs that induce apoptosis of endothelial cells, drugs that induce apoptosis of endothelial cell, and drugs that inhibit cell migration of endothelial cells. Also contemplated by the method of the present invention are low molecular weight EGFR inhibitors (epidermal growth factor receptor antagonists) such as erlotinib, gefitinib, and lapatinib. Moreover, also contemplated are endostatin (O'Reilly et al. (1997) Cell 88: 277-285), angiostatin (O'Reilly et al. (1994) Cell 79: 315-328).

It is known in the art, that antibodies against PlGF and antagonists of PlGF (PlGF: placental growth factor) are anti-angiogenic. However, antibodies were shown to inhibit growth of vessels in tumors but, presumably, not to have significant adverse side effects on the cardiovascular system (see Fischer et al., 2007, Cell, 131, 463-475). Therefore, anti-angiogenesis therapy in the context of the present invention, preferably, does not include administration of antagonists of PlGF, more preferably, the term does not include administration of an antibody that specifically binds PlGF.

The term "sample" refers to a sample of a body fluid, to a sample of separated cells or to a sample from a tissue or an organ. Samples of body fluids can be obtained by well known techniques and include, preferably, samples of blood, plasma, serum, or urine, more preferably, samples of blood, plasma or serum. Tissue or organ samples may be obtained from any tissue or organ by, e.g., biopsy. Separated cells may be obtained from the body fluids or the tissues or organs by separating techniques such as centrifugation or cell sorting. Preferably, cell-, tissue- or organ samples are obtained from those cells, tissues or organs which express or produce the peptides referred to herein.

The method of the present invention is for subjects who shall start anti-angiogenesis therapy. Accordingly, the sample is preferably obtained shortly before an anti-angiogenic therapy shall be initiated. It is particularly contemplated to obtain said sample not more that one day, not more than three days, not more than one week, and, more preferably, not more than one month before the anti-angiogenic therapy shall be initiated.

The term "cardiac troponin" refers to all troponin isoforms expressed in cells of the heart and, preferably, the subendocardial cells. These isoforms are well characterized in the art as described, e.g., in Anderson 1995, Circulation Research, vol. 76, no. 4: 681-686 and Ferrieres 1998, Clinical Chemistry, 44: 487-493. Preferably, cardiac troponin refers to troponin T and/or troponin I. The most preferred cardiac troponin in the context of the present invention is troponin T.

Amino acid sequences for human troponin T and human troponin I are disclosed in Anderson, loc cit and Ferrieres 1998, Clinical Chemistry, 44: 487-493. The term "cardiac troponin" encompasses also variants of the aforementioned specific troponins, i.e., preferably, of Tropoinin T or troponin I. Such variants have at least the same essential biological and immunological properties as the specific cardiac troponins. In particular, they share the same essential biological and immunological properties if they are detectable by the same specific assays referred to in this specification, e.g., by ELISA Assays using polyclonal or monoclonal antibodies specifically recognizing the cardiac troponins. Moreover, it is to be understood that a variant as referred to in accordance with the present invention shall have an amino acid sequence which differs due to at least one amino acid substitution, deletion and/or addition wherein the amino acid sequence of the variant is still, preferably, at least 50%, 60%, 70%, 80%, 85%, 90%, 92%, 95%, 97%, 98%, or 99% identical with the amino sequence of the specific troponin. The degree of identity between two amino acid sequences can be determined by algorithms well known in the art. Preferably, the degree of identity is to be determined by comparing two optimally aligned sequences over a comparison window, where the fragment of amino acid sequence in the comparison window may comprise additions or deletions (e.g., gaps or overhangs) as compared to the reference sequence (which does not comprise additions or deletions) for optimal alignment. The percentage is calculated by determining the number of positions at which the identical amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local homology algorithm of Smith and Waterman Add. APL. Math. 2:482 (1981), by the homology alignment algorithm of Needleman and Wunsch J. Mol. Biol. 48:443 (1970), by the search for similarity method of Pearson and Lipman Proc. Natl. Acad. Sci. (USA) 85: 2444 (1988), by computerized implementations of these algorithms (GAP, BESTFIT, BLAST, PASTA, and TFASTA in the Wisconsin Genetics Software Package, Genetics Computer Group (GCG), 575 Science Dr., Madison, Wis.), or by visual inspection. Given that two sequences have been identified for comparison, GAP and BESTFIT are preferably employed to determine their optimal alignment and, thus, the degree of identity. Preferably, the default values of 5.00 for gap weight and 0.30 for gap weight length are used. Variants referred to above may be allelic variants or any other species specific homologs, paralogs, or orthologs. Moreover, the variants referred to herein include fragments of the specific polypeptides or the aforementioned types of variants as long as these fragments have the essential immunological and biological properties as referred to above. Such fragments may be, e.g., degradation products of the polypeptides. Further included are variants which differ due to posttranslational modifications such as phosphorylation or myristylation.

Determining the amount of the peptides or polypeptides referred to in this specification relates to measuring the amount or concentration, preferably semi-quantitatively or quantitatively. Measuring can be done directly or indirectly. Direct measuring relates to measuring the amount or concentration of the peptide or polypeptide based on a signal which is obtained from the peptide or polypeptide itself and the intensity of which directly correlates with the number of molecules of the peptide present in the sample. Such a signal—sometimes referred to herein as intensity signal—may be obtained, e.g., by measuring an intensity value of a specific physical or chemical property of the peptide or polypeptide. Indirect measuring includes measuring of a signal obtained from a secondary component (i.e. a component not being the peptide or polypeptide itself) or a biological read out system, e.g., measurable cellular responses, ligands, labels, or enzymatic reaction products.

In accordance with the present invention, determining the amount of a peptide or polypeptide can be achieved by all known means for determining the amount of a peptide in a sample. Said means comprise immunoassay devices and methods which may utilize labeled molecules in various sandwich, competition, or other assay formats. Said assays will develop a signal which is indicative for the presence or absence of the peptide or polypeptide. Moreover, the signal strength can, preferably, be correlated directly or indirectly (e.g. reverse-proportional) to the amount of polypeptide present in a sample. Further suitable methods comprise measuring a physical or chemical property specific for the peptide or polypeptide such as its precise molecular mass or NMR spectrum. Said methods comprise, preferably, biosensors, optical devices coupled to immunoassays, biochips, analytical devices such as mass-spectrometers, NMR-analyzers, or chromatography devices. Further, methods include micro-plate ELISA-based methods, fully-automated or robotic immunoassays (available for example on Elecsys™ analyzers), CBA (an enzymatic Cobalt Binding Assay, available for example on Roche-Hitachi™ analyzers), and latex agglutination assays (available for example on Roche-Hitachi™ analyzers).

Preferably, determining the amount of a peptide or polypeptide comprises the steps of (a) contacting a cell capable of eliciting a cellular response the intensity of which is indicative of the amount of the peptide or polypeptide with the peptide or polypeptide for an adequate period of time, (b) measuring the cellular response. For measuring cellular responses, the sample or processed sample is, preferably, added to a cell culture and an internal or external cellular response is measured. The cellular response may include the measurable expression of a reporter gene or the secretion of a substance, e.g. a peptide, polypeptide, or a small molecule. The expression or substance shall generate an intensity signal which correlates to the amount of the peptide or polypeptide.

Also preferably, determining the amount of a peptide or polypeptide comprises the step of measuring a specific intensity signal obtainable from the peptide or polypeptide in the sample. As described above, such a signal may be the signal intensity observed at an m/z variable specific for the peptide or polypeptide observed in mass spectra or a NMR spectrum specific for the peptide or polypeptide.

Determining the amount of a peptide or polypeptide may, preferably, comprises the steps of (a) contacting the peptide with a specific ligand, (b) (optionally) removing non-bound ligand, (c) measuring the amount of bound ligand. The bound ligand will generate an intensity signal. Binding according to the present invention includes both covalent and non-covalent binding. A ligand according to the present invention can be any compound, e.g., a peptide, polypeptide, nucleic acid, or small molecule, binding to the peptide or polypeptide described herein. Preferred ligands include antibodies, nucleic acids, peptides or polypeptides such as receptors or binding partners for the peptide or polypeptide and fragments thereof comprising the binding domains for the peptides, and aptamers, e.g. nucleic acid or peptide aptamers. Methods to prepare such ligands are well-known in the art. For example, identification and production of suitable antibodies or aptamers is also offered by commercial suppliers. The person skilled in the art is familiar with methods to develop derivatives of such ligands with higher affinity or specificity. For example, random mutations can be introduced into the nucleic acids, peptides or polypeptides. These derivatives can then be tested for binding according to screening procedures known in the art, e.g. phage display.

Antibodies as referred to herein include both polyclonal and monoclonal antibodies, as well as fragments thereof, such as Fv, Fab and F(ab)$_2$ fragments that are capable of binding antigen or hapten. The present invention also includes single chain antibodies and humanized hybrid antibodies wherein amino acid sequences of a non-human donor antibody exhibiting a desired antigen-specificity are combined with sequences of a human acceptor antibody. The donor sequences will usually include at least the antigen-binding amino acid residues of the donor but may comprise other structurally and/or functionally relevant amino acid residues of the donor antibody as well. Such hybrids can be prepared by several methods well known in the art. Preferably, the ligand or agent binds specifically to the peptide or polypeptide. Specific binding according to the present invention means that the ligand or agent should not bind substantially to ("cross-react" with) another peptide, polypeptide or substance present in the sample to be analyzed. Preferably, the specifically bound peptide or polypeptide should be bound with at least 3 times higher, more preferably at least 10 times higher and even more preferably at least 50 times higher affinity than any other relevant peptide or polypeptide. Non-specific binding may be tolerable, if it can still be distinguished and measured unequivocally, e.g. according to its size on a Western Blot, or by its relatively higher abundance in the sample. Binding of the ligand can be measured by any method known in the art. Preferably, said method is semi-quantitative or quantitative. Suitable methods are described in the following.

First, binding of a ligand may be measured directly, e.g. by NMR or surface plasmon resonance.

Second, if the ligand also serves as a substrate of an enzymatic activity of the peptide or polypeptide of interest, an enzymatic reaction product may be measured (e.g. the amount of a protease can be measured by measuring the amount of cleaved substrate, e.g. on a Western Blot). Alternatively, the ligand may exhibit enzymatic properties itself and the "ligand/peptide or polypeptide" complex or the ligand which was bound by the peptide or polypeptide, respectively, may be contacted with a suitable substrate allowing detection by the generation of an intensity signal. For measurement of enzymatic reaction products, preferably the amount of substrate is saturating. The substrate may also be labeled with a detectable label prior to the reaction. Preferably, the sample is contacted with the substrate for an adequate period of time. An adequate period of time refers to the time necessary for a detectable, preferably measurable, amount of product to be produced. Instead of measuring the amount of product, the time necessary for appearance of a given (e.g. detectable) amount of product can be measured.

Third, the ligand may be coupled covalently or non-covalently to a label allowing detection and measurement of the ligand. Labelling may be done by direct or indirect methods. Direct labelling involves coupling of the label directly (covalently or non-covalently) to the ligand. Indirect labelling involves binding (covalently or non-covalently) of a secondary ligand to the first ligand. The secondary ligand should specifically bind to the first ligand. Said secondary ligand may be coupled with a suitable label and/or be the target (receptor) of tertiary ligand binding to the secondary ligand. The use of secondary, tertiary or even higher order ligands is often used to increase the signal. Suitable secondary and higher order ligands may include antibodies, secondary antibodies, and the well-known streptavidin-biotin system (Vector Laboratories, Inc.). The ligand or substrate may also be "tagged" with one or more tags as known in the art. Such tags may then be targets for higher order ligands. Suitable tags include biotin, digoxygenin, His-Tag, Glutathion-S-Transferase, FLAG, GFP, myc-tag, influenza A virus haemagglutinin (HA), maltose binding protein, and the like. In the case of a peptide or polypeptide, the tag is preferably at the N-terminus and/or C-terminus. Suitable labels are any labels detectable by an appropriate detection method. Typical labels include gold particles, latex beads, acridan ester, luminol, ruthenium, enzymatically active labels, radioactive labels, magnetic labels ("e.g. magnetic beads", including paramagnetic and superparamagnetic labels), and fluorescent labels. Enzymatically active labels include e.g. horseradish peroxidase, alkaline phosphatase, beta-Galactosidase, Luciferase, and derivatives thereof. Suitable substrates for detection include di-amino-benzidine (DAB), 3,3'-5,5'-tetramethylbenzidine, NBT-BCIP (4-nitro blue tetrazolium chloride and 5-bromo-4-chloro-3-indolyl-phosphate, available as ready-made stock solution from Roche Diagnostics), CDP-Star™ (Amersham Biosciences), ECF™ (Amersham Biosciences). A suitable enzyme-substrate combination may result in a colored reaction product, fluorescence or chemoluminescence, which can be measured according to methods known in the art (e.g. using a light-sensitive film or a suitable camera system). As for measuring the enzymatic reaction, the criteria given above apply analogously. Typical fluorescent labels include fluorescent proteins (such as GFP and its derivatives), Cy3, Cy5, Texas Red, Fluorescein, and the Alexa dyes (e.g. Alexa 568). Further fluorescent labels are available e.g. from Molecular Probes (Oregon). Also the use of quantum dots as fluorescent labels is contemplated. Typical radioactive labels include 35S, 125I, 32P, 33P and the like. A radioactive label can be detected by any method known and appropriate, e.g. a light-sensitive film or a phosphor imager. Suitable measurement methods according the present invention also include precipitation (particularly immunoprecipitation), electrochemiluminescence (electro-generated chemiluminescence), RIA (radioimmunoassay), ELISA (enzyme-linked immunosorbent assay), sandwich enzyme immune tests, electrochemiluminescence sandwich immunoassays (ECLIA), dissociation-enhanced lanthanide fluoro immuno assay (DELFIA), scintillation proximity assay (SPA), turbidimetry, nephelometry, latex-enhanced turbidimetry or nephelometry, or solid phase immune tests. Further methods known in the art (such as gel electrophoresis, 2D gel electrophoresis, SDS polyacrylamid gel electrophoresis (SDS-PAGE), Western Blotting, and mass spectrometry), can be used alone or in combination with labelling or other detection methods as described above.

The amount of a peptide or polypeptide may be, also preferably, determined as follows: (a) contacting a solid support comprising a ligand for the peptide or polypeptide as specified above with a sample comprising the peptide or polypeptide and (b) measuring the amount peptide or polypeptide which is bound to the support. The ligand, preferably chosen from the group consisting of nucleic acids, peptides, polypeptides, antibodies and aptamers, is preferably present on a solid support in immobilized form. Materials for manufacturing solid supports are well known in the art and include, inter alia, commercially available column materials, polystyrene beads, latex beads, magnetic beads, colloid metal particles, glass and/or silicon chips and surfaces, nitrocellulose strips, membranes, sheets, duracytes, wells and walls of reaction trays, plastic tubes etc. The ligand or agent may be bound to many different carriers. Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for the purposes of the invention. Suitable methods for fixing/immobilizing said ligand are well known and include, but are not limited to ionic, hydrophobic, covalent interactions and the like. It is also contemplated to use "suspension arrays" as arrays according to the present invention (Nolan 2002, Trends Biotechnol. 20(1):9-12). In such suspension arrays, the carrier, e.g. a microbead or microsphere, is present in suspension. The array consists of different microbeads or microspheres, possibly labeled, carrying different ligands. Methods of producing such arrays, for example based on solid-phase chemistry and photo-labile protective groups, are generally known (U.S. Pat. No. 5,744,305).

The term "amount" as used herein encompasses the absolute amount of a polypeptide or peptide, the relative amount or concentration of the polypeptide or peptide as well as any value or parameter which correlates thereto or can be derived therefrom. Such values or parameters comprise intensity signal values from all specific physical or chemical properties obtained from the peptides by direct measurements, e.g., intensity values in mass spectra or NMR spectra. Moreover, encompassed are all values or parameters which are obtained by indirect measurements specified elsewhere in this description, e.g., response levels determined from biological read out systems in response to the peptides or intensity signals obtained from specifically bound ligands. It is to be understood that values correlating to the aforementioned amounts or parameters can also be obtained by all standard mathematical operations.

The term "comparing" as used herein encompasses comparing the amount of the peptide or polypeptide comprised by the sample to be analyzed with an amount of a suitable reference source specified elsewhere in this description. It is to be understood that comparing as used herein refers to a comparison of corresponding parameters or values, e.g., an absolute amount is compared to an absolute reference amount while a concentration is compared to a reference concentration or an intensity signal obtained from a test sample is compared to the same type of intensity signal of a reference sample. The comparison referred to in step (b) of the method of the present invention may be carried out manually or computer assisted. For a computer assisted comparison, the value of the determined amount may be compared to values corresponding to suitable references which are stored in a database by a computer program. The computer program may further evaluate the result of the comparison, i.e. automatically provide the desired assessment in a suitable output format. Based on the comparison of the amount determined in step a) and the reference amount, it is possible to assess whether a subject is susceptible to anti-angiogenesis therapy or not. Therefore, the reference amount is to be chosen so that either a difference or a similarity in the compared amounts allows identifying those subjects which are susceptible to anti-angiogenesis therapy.

Accordingly, the term "reference amounts" as used herein refers to amounts of the polypeptides which allows for identifying a subject being susceptible or not being susceptible to anti-angiogenesis therapy. Accordingly, the reference may either be derived from (i) a subject known to be susceptible to anti-angiogenesis therapy (particularly a subject whose cancer was successfully treated and who did not suffer from an adverse side effect such as heart failure and/or a cardiovascular event of said anti-angiogenesis therapy) or (ii) a subject which is known not to be susceptible to anti-angiogenesis therapy (e.g. a subject who suffered from an adverse side effect of said therapy such heart failure and/or a cardiovascular event).

Moreover, the reference amounts, preferably, define thresholds. Suitable reference amounts or threshold amounts may be determined by the method of the present invention from a reference sample to be analyzed together, i.e. simultaneously or subsequently, with the test sample. A preferred reference amount serving as a threshold may be derived from the upper limit of normal (ULN), i.e. the upper limit of the physiological amount to be found in a population of subjects (e.g. patients enrolled for a clinical trial). The ULN for a given population of subjects can be determined by various well known techniques.

More preferably, a reference will be obtained by determining the values for the at least one characteristic feature for a group of reference subjects, i.e. a group of subjects known to be susceptible to anti-angiogenesis therapy, a group of subjects known not to be susceptible to anti-angiogenesis therapy, a population comprising the subject to be investigated and calculating the reference by appropriate statistic measures including those referred to elsewhere herein, such as median, average, quantiles, PLS-DA, logistic regression methods, random forest classification or others that give a threshold value. The threshold value should take the desired clinical settings of sensitivity and specificity of the diagnostic and prognostic test into consideration.

Thus, the reference amount defining a threshold amount for a cardiac troponin, and preferably, for troponin T as referred to in accordance with the present invention is, preferably, 7 pg/ml, and, more preferably, 30 or 20 pg/ml and, even more preferably, 10 pg/ml.

Preferably, an amount of a cardiac troponin lower than the reference amount for said cardiac troponin indicates that said subject is susceptible to anti-angiogenesis therapy.

Preferably, an amount of a cardiac troponin larger than the reference amount for said cardiac troponin indicates that said subject is not susceptible to anti-angiogenesis therapy. For said subject a therapy other than an anti-angiogenesis therapy shall be considered. Also contemplated by the present invention is that a subject who is not susceptible to anti-angiogenesis therapy, is preferably, susceptible to a therapy with a PlGF antagonist, preferably with an antibody against PlGF (PlGF: Placental Growth Factor, see comment on PlGF herein). Therefore, the method of the present invention, in one embodiment, allows to differentiate whether a subject is eligible to anti-angiogenesis therapy or therapy with a PlGF antibody.

Tumor patients treated with anti-angiogenic pharmaceuticals are at increased risk for acute cardiovascular events and heart failure (see above). It was a finding of the studies underlying the present invention that determining the amount of a cardiac troponin T and comparing the thus determined amount to a reference amount, is required for reliably identify those tumor patients which are susceptible to anti-angiogenesis therapy or which are not susceptible to anti-angiogenesis therapy.

Experiments carried out in the context of the present invention strongly suggest that subjects with increased levels of a cardiac troponin shall not be treated with anti-angiogenic pharmaceuticals since these patients are at elevated risk of suffering from an acute cardiovascular event in the future. Anti-angiogenic drugs do not only block the formation of new blood vessels in tumors, they also block the formation of new vessels in atherosclerotic regions in which a new formation is desired. The results of the studies carried out in the context of the present invention indicate that individuals with increased levels of the biomarkers referred to herein, are at increased risk of acute cardiovascular events when taking drugs that prevent the growth and/or formation of new blood vessels.

Specifically, the amount of troponin T was determined in serum samples of a patient cohort comprising patients with various tumors was determined. The experiments showed that the prevalence of cardiovascular complications in tumor patients is much higher than suspected and that there is a clear need to identify those subjects which are less likely to benefit from anti-angiogenesis therapy particularly, those subjects with previously undetected cardiovascular complications. In case the patient turns out to be not susceptible for an anti-angiogenesis therapy, a cost intensive therapy that would put said subject at risk can be avoided.

Moreover, the method of the present invention is advantageous since it can be implemented in portable systems, such as test strips.

Taken together patients with an increased troponin T amount are at increased risk of suffering from heart failure and/or acute cardiovascular events when receiving anti-angiogenic medication (due to said therapy). Patients with an amount that are not increased are not at elevated risk of suffering from heart failure and/or acute cardiovascular events when receiving anti-angiogenic medication.

Moreover, in addition to troponin T, also the amount of NT-proBNP was determined in samples of the patients referred to above. It was shown, that the determination of NT-proBNP adds further diagnostic and prognostic value. The results indicate that subjects with increased levels of both NT-proBNP and troponin T are at increased risk of suffering from a cardiovascular event when on medication with an anti-angiogenesis therapy. Thus, when determining both a natriuretic peptide and cardiac troponin a statistically more significant proportion of subjects can be correctly identified compared to determining only cardiac troponin as a single marker alone. However, the determination of a cardiac troponin alone already allows identifying subjects with a high significance.

Accordingly, the method of the present invention further may comprise determining the amount of a natriuretic peptide in a sample of the patient and comparing the, thus, determined amount to a reference amount.

The term "natriuretic peptide" comprises Atrial Natriuretic Peptide (ANP)-type and Brain Natriuretic Peptide (BNP)-type peptides and variants thereof having the same predictive potential. Natriuretic peptides according to the present invention comprise ANP-type and BNP-type peptides and variants thereof (see e.g. Bonow, 1996, Circulation 93: 1946-1950). ANP-type peptides comprise pre-proANP, proANP, NT-proANP, and ANP. BNP-type peptides comprise pre-proBNP, proBNP, NT-proBNP, and BNP. The pre-pro peptide (134 amino acids in the case of pre-proBNP) comprises a short signal peptide, which is enzymatically cleaved off to release the pro peptide (108 amino acids in the case of proBNP). The pro peptide is further cleaved into an N-terminal pro peptide (NT-pro peptide, 76 amino acids in case of NT-proBNP) and the active hormone (32 amino acids in the case of BNP, 28 amino acids in the case of ANP). Preferred natriuretic peptides according to the present invention are NT-proANP, ANP, NT-proBNP, BNP, and variants thereof. ANP and BNP are the active hormones and have a shorter half-life than their respective inactive counterparts, NT-proANP and NT-proBNP. BNP is metabolised in the blood, whereas NT-proBNP circulates in the blood as an intact molecule and as such is eliminated renally. The in-vivo half-life of NTproBNP is 120 min longer than that of BNP, which is 20 min (Smith 2000, J. Endocrinol. 167: 239-46.). Preanalytics are more robust with NT-proBNP allowing easy transportation of the sample to a central laboratory (Mueller 2004, Clin Chem Lab Med 42: 942-4.). Blood samples can be stored at room temperature for several days or may be mailed or shipped without recovery loss. In contrast, storage of BNP for 48 hours at room temperature or at 4° Celsius leads to a concentration loss of at least 20% (Mueller loc.cit.; Wu 2004, Clin Chem 50: 867-73.). Therefore, depending on the time-course or properties of interest, either measurement of the active or the inactive forms of the natriuretic peptide can be advantageous. More preferred natriuretic peptides according to the present invention are BNP and NT-proBNP or variants thereof. The most preferred natriuretic peptides according to the present invention are NT-proBNP or variants thereof. As briefly discussed above, the human NT-proBNP, as referred to in accordance with the present invention, is a polypeptide comprising, preferably, 76 amino acids in length corresponding to the N-terminal portion of the human NT-proBNP molecule. The structure of the human BNP and NT-proBNP has been described already in detail in the prior art, e.g., WO 02/089657, WO 02/083913 or Bonow loc. cit. Preferably, human NT-proBNP as used herein is human NT-proBNP as disclosed in EP 0 648 228 B1. These prior art documents are herewith incorporated by reference with respect to the specific sequences of NT-proBNP and variants thereof disclosed therein. The NT-proBNP referred to in accordance with the present invention further encompasses allelic and other variants of said specific sequence for human NT-proBNP discussed above. Specifically, envisaged are variant polypeptides which are on the amino acid level at least 60% identical, more preferably at least 70%, at least 80%, at least 90%, at least 95%, at least 98% or at least 99% identical, to human NT-proBNP. How to determine the degree of identity is specified elsewhere herein. Substantially similar and also envisaged are proteolytic degradation products which are still recognized by the diagnostic means or by ligands directed against the respective full-length peptide. Also encompassed are variant polypeptides having amino acid deletions, substitutions, and/or additions compared to the amino acid sequence of human NT-proBNP as long as the polypeptides have NT-proBNP properties. NT-proBNP properties as referred to herein are immunological and/or biological properties. Preferably, the NT-proBNP variants have immunological properties (i.e. epitope composition) comparable to those of NT-proBNP. Thus, the variants shall be recognizable by the aforementioned means or ligands used for determination of the amount of the natriuretic peptides. Biological and/or immunological NT-proBNP properties can be detected by the assay described in Karl et al. (Karl 1999, Scand J Clin Invest 230:177-181), Yeo et al. (Yeo 2003, Clinica Chimica Acta 338:107-115). Variants also include posttranslationally modified peptides such as glycosylated peptides. Further, a variant in accordance with the present invention is also a peptide or polypeptide which has been modified after collection of the sample, for example by covalent or non-covalent attachment of a label, particularly a radioactive or fluorescent label, to the peptide.

How to determine suitable reference amounts is described herein above.

Preferably, a reference amount defining a threshold amount for natriuretic peptide, and preferably, for NT-proBNP, as referred to in accordance with the present invention is 250 pg/ml, 400, 500 or 1000 pg/ml. Of the aforementioned thresholds for NT-proBNP, 250 pg/ml is the most preferred threshold (preferably in a serum sample).

Preferably, an amount of a cardiac troponin lower than the reference amount for said cardiac troponin, and an amount a natriuretic peptide lower than the reference amount for said natriuretic peptide indicates that said subject is susceptible to anti-angiogenesis therapy.

Preferably, an amount of a cardiac troponin larger than the reference amount for said cardiac troponin, and an amount a natriuretic peptide larger than the reference amount for said natriuretic peptide indicates that said subject is not susceptible to anti-angiogenesis therapy. For said subject a therapy other than an anti-angiogenesis therapy shall be considered.

If, in a sample of a subject, (i) the amount of a cardiac troponin is larger than the reference amount for said cardiac troponin and the amount of a natriuretic peptide is lower than the reference amount for a natriuretic peptide, or (ii) the amount of a cardiac troponin is lower than the reference amount for said cardiac troponin and the amount of a natriuretic peptide is larger than the reference amount for a natriuretic peptide, said subject needs to be carefully monitored if said subject is being treated with anti-angiogenic drugs.

Moreover, the present invention also relates to a method for predicting the risk of an acute cardiovascular event as a consequence of a future anti-angiogenesis therapy, comprising the steps of
  a) determining the amount of a cardiac troponin in a sample of a subject,
  b) comparing the amount of a cardiac troponin as determined in step a) with suitable reference amount for a cardiac troponin, and
  c) predicting the risk in said subject of an acute cardiovascular event for a subject of a future anti-angiogenic therapy (preferably, of a future intake of anti-angiogenic drugs).

The term "predicting" as used to assessing the probability according to which said subject will develop a cardiovascular event, preferably an acute cardiovascular event within a defined time window (predictive window), if said subject will take anti-angiogenic drugs (in the future). Thus, the aforementioned method is, particularly, advantageous for the assessment of risks for subjects who are candidates for receiving anti-angiogenic drugs. Accordingly, the sample is preferably obtained shortly before an anti-angiogenic therapy shall be initiated. It is particularly contemplated to obtain said sample not more that one day, not more than three days, not more than one week, and, more preferably, not more than one month before the anti-angiogenic therapy shall be initiated.

The predictive window is an interval in which the subject will develop a cardiovascular event or will die according to the predicted probability (if taking anti-angiogenic drugs). The predictive window may be the entire remaining lifespan of the subject upon analysis by the method of the present invention. Preferably, however, the predictive window is an interval of one month, six months or one, two, three, four, five or ten years after starting an anti-angiogenic therapy. As will be understood by those skilled in the art, such an assessment is usually not intended to be correct for 100% of the subjects to be analyzed. The term, however, requires that the assessment will be valid for a statistically significant portion of the subjects to be analyzed. Whether a portion is statistically significant can be determined without further ado by the person skilled in the art using various well known statistic evaluation tools, e.g., determination of confidence intervals, p-value determination, Student's t-test, Mann-Whitney test, etc. Details are found in Dowdy and Wearden, Statistics for Research, John Wiley & Sons, New York 1983. Preferred confidence intervals are at least 90%, at least 95%, at least 97%, at least 98% or at least 99%. The p-values are, preferably, 0.1, 0.05, 0.01, 0.005, or 0.0001. Preferably, the probability envisaged by the present invention allows that the prediction will be correct for at least 60%, at least 70%, at least 80%, or at least 90% of the subjects of a given cohort.

The term "predicting the risk of an acute cardiovascular event" as used herein means that the subject to be analyzed by the method of the present invention is allocated either into the group of subjects of a population having a normal, i.e. non-elevated and, thus, average risk for developing an acute cardiovascular event, or into a group of subjects having an elevated risk, or into a group of subjects having a significantly elevated risk. An elevated risk as referred to in accordance with the present invention also means that the risk of developing a cardiovascular event within a predetermined predictive window is elevated for a subject with respect to the average risk for a cardiovascular event in a population of subjects as defined herein. Preferably, for a predictive window of one year, the average risk is within the range 1.5 and 2.0%, preferably, lower than 2.0%. An elevated risk as used herein, preferably, relates to a risk of more than 2.0%, preferably, more than 4.0%, and, most preferably within 3.0% and 5.0%, with respect to a predictive window of one year. A significantly elevated risk as used herein, preferably relates to a risk more than 5.0%, preferably within the range of 5.0% and 8.0%, or even higher with respect to a predictive window of one year.

Acute cardiovascular events are, preferably, acute coronary syndromes (ACS). ACS patients can show unstable angina pectoris (UAP) or myocardial infarction (MI). MI can be an ST-elevation MI (STEMI) or a non-ST-elevated MI (NSTEMI). The occurring of an ACS can be followed by a left ventricular dysfunction (LVD) and symptoms of heart failure. How to diagnose an acute cardiovascular event is well known in the art.

Preferably, an amount of a cardiac troponin in a sample of a subject larger than the reference amount is indicative for a subject being at elevated risk of an acute cardiovascular event, if said subject will be on anti-angiogenesis therapy. For preferred reference amounts see elsewhere herein.

Preferably, an amount of a cardiac troponin in a sample of a subject lower than the reference amount is indicative for a subject not being at elevated risk, and, thus, being at average risk for an acute cardiovascular event (if being on anti-angiogenesis therapy in the future).

If also a natriuretic peptide is determined, the following applies:

Preferably, an amount of a cardiac troponin lower than the reference amount for said cardiac troponin, and an amount of a natriuretic peptide lower than the reference amount for said natriuretic peptide is indicative for a subject not being at elevated risk, and, thus, being on average risk for an acute cardiovascular event (for preferred reference amounts see herein above).

Preferably, an amount of a cardiac troponin larger than the reference amount for said cardiac troponin, and an amount of a natriuretic peptide larger than the reference amount for said natriuretic peptide is indicative for a subject being at elevated risk of an acute cardiovascular event (for preferred reference amounts see herein above).

By carrying out the steps of the aforementioned method, also the risk of suffering from hypertension, heart failure, or other vascular events (particularly, stroke, peripheral arterial disease, and/or abdominal angina), preferably, as a consequence of the therapy can be predicted for a subject as defined above.

Moreover, the present invention relates to a device for identifying a subject being susceptible to anti-angiogenesis therapy comprising means for determining the amount of a cardiac troponin (preferably troponin T) in a sample of a subject in need of an anti-angiogenesis therapy, and means for comparing the amount determined by said means to a reference amount for a cardiac troponin, whereby a subject being susceptible to anti-angiogenesis therapy is identified and/or whereby the risk of an acute cardiovascular event in a subject of being of a future anti-angiogenesis therapy is predicted.

Preferably, said device further comprises means for determining the amount of a natriuretic peptide, in particular of NT-proBNP, in said sample of said subject and means for comparing the amount determined by said means to a reference amount for a natriuretic peptide.

The term "device" as used herein relates to a system of means comprising at least the aforementioned means operatively linked to each other as to allow the identification of subjects susceptible to anti-angiogenesis therapy. Preferred means for determining the amount of a cardiac troponin and a natriuretic peptide, and means for carrying out the comparison are disclosed above in connection with the method of the invention. How to link the means in an operating manner will depend on the type of means included into the device. For example, where means for automatically determining the amount of the peptides are applied, the data obtained by said automatically operating means can be processed by, e.g., a computer program in order to obtain the desired results. Preferably, the means are comprised by a single device in such a case. Said device may accordingly include an analyzing unit for the measurement of the amount of the peptides or polypeptides in an applied sample and a computer unit for processing the resulting data for the evaluation. Alternatively, where means such as test strips are used for determining the amount of the peptides or polypeptides, the means for comparison may comprise control strips or tables allocating the determined amount to a reference amount. The test strips are, preferably, coupled to a ligand which specifically binds to the peptides or polypeptides referred to herein. The strip or device, preferably, comprises means for detection of the binding of said peptides or polypeptides to the ligand. Preferred means for detection are disclosed in connection with embodiments relating to the method of the invention above. In such a case, the means are operatively linked in that the user of the system brings together the result of the determination of the amount and the diagnostic or prognostic value thereof due to the instructions and interpretations given in a manual. The means may appear as separate devices in such an embodiment and are, preferably, packaged together as a kit. The person skilled in the art will realize how to link the means without further ado. Preferred devices are those which can be applied without the particular knowledge of a specialized clinician, e.g., test strips or electronic devices which merely require loading with a sample. The results may be given as output of raw data which need interpretation by the clinician. Preferably, the output of the device is, however, processed, i.e. evaluated, raw data the interpretation of which does not require a clinician. Further preferred devices comprise the analyzing units/devices (e.g., biosensors, arrays, solid supports coupled to ligands specifically recognizing the polypeptide whose amount shall be determined, Plasmon surface resonance devices, NMR spectrometers, mass-spectrometers etc.) or evaluation units/devices referred to above in accordance with the method of the invention.

Also envisaged by the present invention is a kit adapted to carry out the method of the present invention, said kit comprising instructions for carrying out the method, and means for determining the amount of a cardiac troponin (preferably troponin T) in a sample of a subject in need of an anti-angiogenesis therapy, and means for comparing the amount determined by said means to a reference amount for a cardiac troponin (preferably troponin T), allowing identifying a subject being susceptible to a anti-angiogenesis therapy and/or predicting the risk of an acute cardiovascular event in a subject of being on anti-angiogenesis therapy (in the future).

Preferably, said kit further comprises means for determining the amount of a natriuretic peptide, in particular of NT-proBNP, in said sample of said subject and means for comparing the amount determined by said means to a reference amount for a natriuretic peptide.

The term "kit" as used herein refers to a collection of the aforementioned compounds, means or reagents of the present invention which may or may not be packaged together. The components of the kit may be comprised by separate vials (i.e. as a kit of separate parts) or provided in a single vial. Moreover, it is to be understood that the kit of the present invention is to be used for practicing the methods referred to herein above. It is, preferably, envisaged that all components are provided in a ready-to-use manner for practicing the methods referred to above. Further, the kit preferably contains instructions for carrying out the methods. The instructions can be provided by a users manual in paper- or electronic form. For example, the manual may comprise instructions for interpreting the results obtained when carrying out the aforementioned methods using the kit of the present invention.

Finally, the present invention, preferably, relates to the use of a cardiac troponin for identifying a subject being susceptible to anti-angiogenesis therapy. More preferably, the present invention relates to the use of a cardiac troponin and a natriuretic peptide for identifying a subject being susceptible to anti-angiogenesis therapy.

All references cited in this specification are herewith incorporated by reference with respect to their entire disclosure content and the disclosure content specifically mentioned in this specification.

The following examples shall merely illustrate the invention. They shall not be construed, whatsoever, to limit the scope of the invention.

Example 1

Determination of Troponin T and NT-proBNP in Serum and Plasma Samples

Troponin T and NT-proBNP were determined in a collective of 324 patients suffering from various forms of tumors. Surprisingly, a majority of tumor patients (56%) had NT-proBNP level larger than 125 pg/ml indicating heart failure. Moreover, 85% of tumor patients had detectable levels of troponin T (levels larger than 1 pg/ml of troponin T indicating necrosis of cardiac tissue. In 29% of the patients even troponin T levels of larger than 10 pg/ml were measured.

Taken together, the results of the study underlying the present invention shows that the determination of a cardiac troponin (and of NT-proBNP) allows identification of subjects being at risk for a cardiovascular event as a consequence of anti-angiogenesis therapy and therefore allows identification of subjects which are susceptible or not susceptible to an anti-angiogenesis therapy.

Example 2

A 59 years old male patient suffers from advanced colorectal cancer. The patient has a history of coronary artery disease, and, therefore, has two implanted stents. The advanced colorectal cancer requires a suitable therapy. The patients is examined, and the amounts of troponin T (11 pg/ml) and NT-proBNP (620 pg/ml) are determined in a serum sample. Moreover, the LVEF is determined (35%) indicating a reduced left ventricular systolic dysfunction. The subject is subsequently subjected to cardiac stress testing. Since the cardiac stress testing only indicates regions in the myocardium with non reversible perfusion defects (and no regions with reversible perfusion defects), a revascularization of the myocardium is not carried out. Treatment with VEGF-inhibitors is initiated. Four month after the start of the therapy, the patient suffers from a myocardial infarction.

Example 3

A 62 years old male patient and previous smoker suffers from a myocardial infarction. Three years later, advanced colorectal cancer is diagnosed necessitating a suitable cancer therapy. The left ventricular ejection fraction (LVEF) is determined by echocardiography (40%) indicating a minor systolic dysfunction. Moreover, the amounts of a troponin T (12 pg/ml) and NT-proBNP (410 pg/ml) are determined in a sample of the patient. The patient is subjected to a cardiac stress test showing that a region of the posterior myocardial wall has a dysfunctional contractility (reversible perfusion defects). Coronary angiography is carried out indicating 80% stenosis of the artery that supplies the region of dysfunctional contractility with blood. Fours weeks after successful revascularization of the affected myocardial regions, troponin T (4 pg/ml) and NT-proBNP (180 pg/ml) are determined again. A therapy with VEGF-inhibitors is started. The patient does not suffer from adverse side effects during the therapy.

Example 4

Levels of troponin T and/or NT-proBNP were determined in serum samples obtained from 27 patients treated with Bevacizumab before the therapy was started and during therapy. In the majority of patients (more than 80%), the levels of the markers remained unchanged, i.e. there was no significant increase indicating that the therapy did not have adverse side effects on the cardiovascular system. In some patients, however, there was a significant increase of the measured markers indicating a risk of cardiovascular complications. Examples are shown herein below.

Patient (ID No: 4201): Samples were obtained at the start of the therapy, as well as 14, 21 and 35 days after the therapy was started (no adverse side effects on the cardiovascular system)

| Patient ID | Sample obtained (d) | Troponin T (pg/ml) | NT-proBNP (pg/ml) |
| --- | --- | --- | --- |
| 4201 | 0 | 4 | 38 |
| 4201 | 14 | 1 | 51 |
| 4201 | 21 | 1 | 26 |
| 4201 | 35 | 1 | 16 |

Patient (ID No: 4208): Troponin T and NT-proBNP 13 and 57 days after the therapy was started. Significant increases of the measured markers were observed indicating a risk of cardiovascular complications.

| Patient ID | Sample obtained (d) | Troponin T (pg/ml) | NT-proBNP (pg/ml) |
| --- | --- | --- | --- |
| 4208 | 13 | 13 | 296 |
| 4208 | 57 | 44 | 844 |

Patient (ID No: 4210): Samples were obtained at the start of the therapy as well as 14 days after the therapy was started. At treatment initiation, the troponin T level was significantly increased (also the NT-proBNP level: 1916 pg/ml). During treatment, there was a further increase of troponin T indicating an enhanced risk of cardiovascular complication.

| Patient ID | Sample obtained (d) | Troponin T (pg/ml) |
| --- | --- | --- |
| 4210 | 0 | 42 |
| 4210 | 14 | 80 |

What is claimed is:

1. A method for identifying whether a subject under consideration for anti-angiogenic therapy may be suitably treated with a vascular endothelial growth factor (VEGF) antagonist, the method comprising:
   conducting an assay to determine an amount of cardiac troponin in a sample from the subject, the assay comprising:
   contacting, in vitro, a portion of a sample from the subject with a specific ligand for a cardiac troponin,
   calculating an amount of the cardiac troponin based on said contacting,
   comparing the calculated amount to a reference amount; and
   identifying treatment of the subject with an anti-angiogenic therapy comprising administration of a VEGF antagonist if the calculated amount of cardiac troponin is lower than the reference amount, and
   initiating either (i) treatment of the subject with an anti-angiogenic therapy that avoids treatment with a VEGF antagonist or (ii) treatment of the subject with a therapy that is not anti-angiogenic if the calculated amount of cardiac troponin is high than the reference amount.

2. The method of claim 1, comprising obtaining the sample from the subject not more than one month before initiating a treatment.

3. The method of claim 1, wherein the subject suffers from cancer.

4. The method of claim 1, wherein the cardiac troponin is troponin T.

5. The method of claim 1, wherein the cardiac troponin is troponin T and the reference amount for troponin T is 10 pg/ml.

6. The method of claim 1, wherein the calculated amount of cardiac troponin is lower than the reference amount, and the method further comprises contacting, in vitro, a portion of a sample from the subject with a specific ligand for a natriuretic peptide, calculating an amount of natriuretic peptide based on the said step of contacting, comparing the amount of natriuretic peptide calculated to a reference amount of natriuretic peptide, and initiating treatment with an anti-angiogenic therapy comprising administration of a VEGF antagonist if the calculated amount of natriuretic peptide is lower than the reference amount of natriuretic peptide, and initiating treatment of the subject with an anti-angiogenic therapy comprising administration of a VEGF antagonist subject to additional monitoring if the calculated amount of natriuretic peptide is greater than the reference amount of natriuretic peptide.

7. The method of claim 6, wherein the natriuretic peptide is N-terminal pro brain natriuretic peptide (NT-proBNP) and the reference amount for NT-proBNP is 250 pg/ml.

8. The method of claim 7, wherein the reference amount of cardiac troponin is 10 pg/ml and the reference amount of NT-proBNP is 250 pg/ml.

9. The method of claim 1, wherein initiating treatment of the subject with a therapy that is not anti-angiogenic comprises administering a PIGF antagonist.

10. The method of claim 1, wherein the calculated amount of cardiac troponin in the subject is higher thatn the reference amount, and wherein the step of treating the subject with a therapy that is not anti-angiogenic comprises treating the subject with a revascularization therapy.

11. The method according to claim 1, wherein the VEGF antagonist comprises an anti-VEGF antibody.

12. The method according to claim 11, wherein the VEGF antibody is selected from bevacizumab and ranibizumab.

* * * * *